(12) United States Patent
Robotti et al.

(10) Patent No.: US 7,396,676 B2
(45) Date of Patent: Jul. 8, 2008

(54) EVANESCENT WAVE SENSOR WITH ATTACHED LIGAND

(75) Inventors: Karla M. Robotti, Mountain View, CA (US); Daniel B. Roitman, Menlo Park, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 269 days.

(21) Appl. No.: 11/143,358

(22) Filed: May 31, 2005

(65) Prior Publication Data

US 2006/0269930 A1 Nov. 30, 2006

(51) Int. Cl.
*C12M 1/34* (2006.01)

(52) U.S. Cl. .......... 435/287.2; 385/12; 385/129; 385/130; 422/82.05; 422/82.11; 435/5; 435/6; 435/7.2; 435/7.32; 435/288.7; 435/808; 436/164; 436/165; 436/524; 436/525; 436/527; 436/532; 436/805

(58) Field of Classification Search .......... 385/12, 385/129, 130; 422/82.05, 82.11; 435/5, 435/7.2, 7.32, 6, 287.2, 288.7, 808; 436/164, 436/165, 524, 525, 527, 532, 805
See application file for complete search history.

(56) References Cited

U.S. PATENT DOCUMENTS

| 5,242,828 A * | 9/1993 | Bergstrom et al. ....... 435/287.1 |
| 2003/0044833 A1 | 3/2003 | Elouard et al. |
| 2004/0124149 A1 | 7/2004 | Egisto |
| 2005/0181497 A1 | 8/2005 | Yukou et al. |
| 2005/0221337 A1 | 10/2005 | Seeberger et al. |

FOREIGN PATENT DOCUMENTS

| EP | 0 220 899 | 5/1987 |
| EP | 1 143 251 | 10/2001 |
| EP | 1 182 450 | 2/2002 |
| WO | WO 02/057422 | 7/2002 |
| WO | WO 03/006676 | 1/2003 |
| WO | WO 03/083477 | 10/2003 |
| WO | WO 2004/055160 | 7/2004 |
| WO | WO 2004/058946 | 7/2004 |
| WO | WO 2005/016971 | 2/2005 |

OTHER PUBLICATIONS

Da Cruz et al., "Study of a self-assembled porphyrin monomolecular layer obtained by metal complexation," Thin Solid Films, Elsevier Switzerland, vol. 349, No. 1-2, (Jul. 30, 1999), pp. 155-161.

(Continued)

*Primary Examiner*—Christopher L Chin

(57) ABSTRACT

The invention in particular embodiments provides an evanescent wave sensor which includes a ligand bound to a sensor substrate via a NCYX linker moiety, as defined herein. Methods of making the subject evanescent wave sensors are also provided which include contacting a first reactive moiety which has an isocyanato (or isothiocyanato) moiety with a second reactive moiety which has an hydroxyl, thiol, or amino moiety, as further described herein. Also provided by the invention are methods in which a subject evanescent wave sensor is contacted with a sample, and binding of analytes in the sample to the sensor is assessed by evanescent wave detection. The invention also provides kits and systems for performing the subject methods.

25 Claims, 2 Drawing Sheets

OTHER PUBLICATIONS

Database Biosis [online] Biosciences Information Service, Philadelphia, PA, US: 2004, Sato Yasunobu et al: "Flow-stress-induced discrimination of a K-ras point mutation by sandwiched polymer microsphere-enhanced surface plasmon reasonance" XP002421823 Database accession No. PREV200400295390 abstract.

Angenendt, "Progress in protein and antibody microarray technology", Drug Discovery Today, vol. 10, No. 7, Apr. 1, 2005, pp. 503-511, XP04871773, p. 507, left-hand column, line 2; table 1.

Pope et al., "New applicatio of silane coupling agents for covalently binding antibodies to glass and cellulose solid supports." Bioconjugate Chemistry, vol. 4, No. 2, 1993, pp. 166-171, XP002421821 pp. 166-167.

Lui et al., "Quartz crystal biosensor for real-time kinetic analysis of interaction between human TNF-alpha and monoclonal antibodies", Sensors and Actuabors B, vol. 99, No. 2-3, 2004, pp. 416-425 XP004505796 pp. 417, right-hand column, paragraph 3; figure 2.

* cited by examiner

EVANESCENT WAVE SENSOR WITH ATTACHED LIGAND

RELATED APPLICATIONS

Related information is disclosed in patent application Ser. No. 11/133,883 entitled "Evanescent Wave Sensor with Attached Ligand" filed May 19, 2005 by Robotti et al.

FIELD OF THE INVENTION

The invention relates generally to sensors for the detection of
analytes. More specifically, the invention relates to evanescent wave sensors having ligands bound to a surface of the sensor.

BACKGROUND OF THE INVENTION

Sensitive and accurate methods for detecting molecular interactions are very desirable for a wide variety of applications, including drug discovery, environmental testing, diagnostics, gene expression analysis, genomics analysis, proteomics and for characterizing the binding of two molecules that are known to bind together. Several optical techniques for measuring molecular interactions at surfaces have been developed based on the evanescent field wave phenomenon.

One technique used is surface plasmon resonance, hereinafter referred to as SPR. The phenomenon of SPR is well known, and reviews may be found in, e.g. Homola, J., et al., Sensors and Actuators B 54: 3-15 (1999); Welford, K., Opt. Quant. Elect. 23:1 (1991); Raether, H., Physics of Thin Films 9: 145 (1977).

Typically, SPR is measured as a dip in intensity of light for a specific wavelength reflected at a specific angle from the interface between an optically transparent material, e.g., glass, and a thin metal film, usually silver or gold, and is dependent on the refractive index of the medium close to the metal surface. A change of the real part of the complex refractive index at the metal surface, such as by the adsorption or binding of material thereto, will cause a corresponding shift in the angle at which SPR occurs, the so-called SPR-angle. For a specific angle of incidence, the SPR is observed as a dip in intensity of light at a specific wavelength, a change in the real part of the refractive index causing a corresponding shift in the wavelength at which SPR occurs. In typical configurations, the medium close to the metal surface includes a sample which alters the refractive index of the medium close to the metal surface dependent upon the composition of the sample.

Three alternative arrangements may be used to couple the light to the interface such that SPR arises. These methods include using a metallized diffraction grating (see H. Raether in "Surface Polaritons", Eds. Agranovich and Mills, North Holland Publ. Comp., Amsterdam, 1982), a metallized glass prism (Kretschmann configuration), or a prism in close contact with a metallized surface on a glass substrate (Otto configuration). In a SPR-based assay, for example, a ligand is bound to the metal surface, and the interaction of this sensing surface with an analyte in a solution in contact with the surface is monitored.

Other optical techniques similar to SPR are Brewster angle reflectometry (BAR) and critical angle reflectometry (CAR). When light is incident at the boundary between two different transparent dielectric media, from the higher to the lower refractive index medium, the internal reflectance varies with angle of incidence for both the s- and p-polarized components. The reflected s-polarized component increases with the angle of incidence, and the p-polarized component shows a minimum reflectance at a specific angle, the Brewster angle. The angle at which both s- and p-polarized light is totally internally reflected is defined as the critical angle. For all angles of incidence greater than the critical angle, total internal reflection (TIR) occurs.

Another optical technique similar to SPR is evanescent wave ellipsometry, described in Azzam, R. M. A., Surface Science 56: 126-133 (1976). In evanescent wave ellipsometry the intensity and polarization ellipse of the light reflected from the interface can be monitored as functions of the angle of incidence, wavelength or time. Under steady state conditions, measurements as a function of wavelength and angle of incidence can provide basic information on the molecular composition and organization of the medium close to the interface. In a dynamic time-varying situation, measurements as a function of time can resolve the kinetics of certain surface changes.

Evanescent wave sensors used in biochemical sensing applications typically have one or more ligands bound at or near the interface. The ligands are capable of selectively binding to the desired analytes. Binding of analytes by the ligands shifts the refractive index of the medium near the interface, thereby affecting the evanescent wave in a detectable fashion. Since the evanescent field wave penetrates only a short distance into the medium near the interface, the conditions for the evanescent wave sensors are relatively insensitive to changes in the bulk medium (distal from the interface). This provides a potential for very selective sensing of analytes based on selective ligand-analyte interactions.

Many methods are known for binding ligands at or near the interface. Representative methods are discussed in, e.g. Homola, J., et al., Sensors and Actuators B 54: 3-15 (1999); U.S. Pat. No. 5,242,828 to Bergstrom et al. (1993); and U.S. Pat. No. 6,738,141 to Thirstrup (2004).

Further literature of interest includes: U.S. Pat. No. 6,027,890 to Ness, et al. (2000); PCT publication WO97/27331; U.S. publication 20020117659; and the following papers: Olejnik et al., Proc. Natl. Acad. Sci. 92:7590-94; Olejnik et al., Meth. Enzymol. 291:135-154 (1998); Zhao et al., Anal. Chem. 74:4259-4268 (2002); Sanford et al., Chem. Mater. 10:1510-20 (1998); Guillier et al., Chem. Rev. 100:2091-2157 (2000); Fong et al., Analytica Chimica Acta 456:201-208 (2002); Ogata et al., Anal. Chem. 74:4702-4708 (2002); Bai et al., Nucl. Acids Res. 32:535-541 (2004); Cooper, Anal. Bioan. Chem 337:843-842 (2003); Homola, J., Anal. Bioan. Chem 337:528-539 (2003); Schultz, Curr. Opin. Biotechnol. 14:13-22 (2003); McDonnell, Curr. Opin. Chem. Biol. 5:572-577 (2001); Borch et al., Anal Chem 76:5243-5248 (2004); and Cui et al., Science 293:1289-1292 (2001).

A need still remains for further methods of providing sensors specific for desired analytes and methods of using such sensors.

SUMMARY OF THE INVENTION

The invention addresses the aforementioned deficiencies in the art, and provides novel methods of making sensors having an attached ligand for specifically binding to an analyte of interest, as well as methods and apparatus for using such sensors.

The invention in particular embodiments provides an evanescent wave sensor which includes a ligand bound to a sensor substrate via an NCYX linker moiety. Methods of making the subject evanescent wave sensors are also provided; the methods include contacting a first reactive moiety having the structure

with a second reactive moiety having the structure

under conditions sufficient to result in a compound having the structure

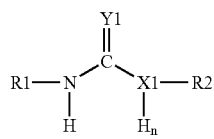

wherein:
one of R1 or R2 is a sensor substrate;
the other of R1 or R2 is selected from a ligand, a linking group bound to a ligand, a functional group for binding a ligand, or a linking group bound to a functional group for binding a ligand;
Y1 is selected from O or S;
X1 is selected from O, N or S, provided that, if Y1 is S, X1 is N;
n equals 1 when X1 is N, or n equals 0 when X1 is S or O; and
m equals n plus 1.

Also provided by the invention are methods in which a subject evanescent wave sensor is contacted with a sample, and binding of analytes in the sample to the sensor is assessed by evanescent wave detection. The invention also provides kits and systems for performing the subject methods.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the instruments, combinations, compositions and methods particularly pointed out in the appended claims.

BRIEF DESCRIPTION OF THE DRAWINGS

These and other features of the invention will be understood from the description of representative embodiments of the method herein and the disclosure of illustrative apparatus for carrying out the method, taken together with the Figures, wherein FIG. 1 schematically illustrates an embodiment of an evanescent wave sensor in accordance with the present invention.

To facilitate understanding, identical reference numerals have been used, where practical, to designate corresponding elements that are common to the Figures. Figure components are not drawn to scale.

DETAILED DESCRIPTION

Figure 1:
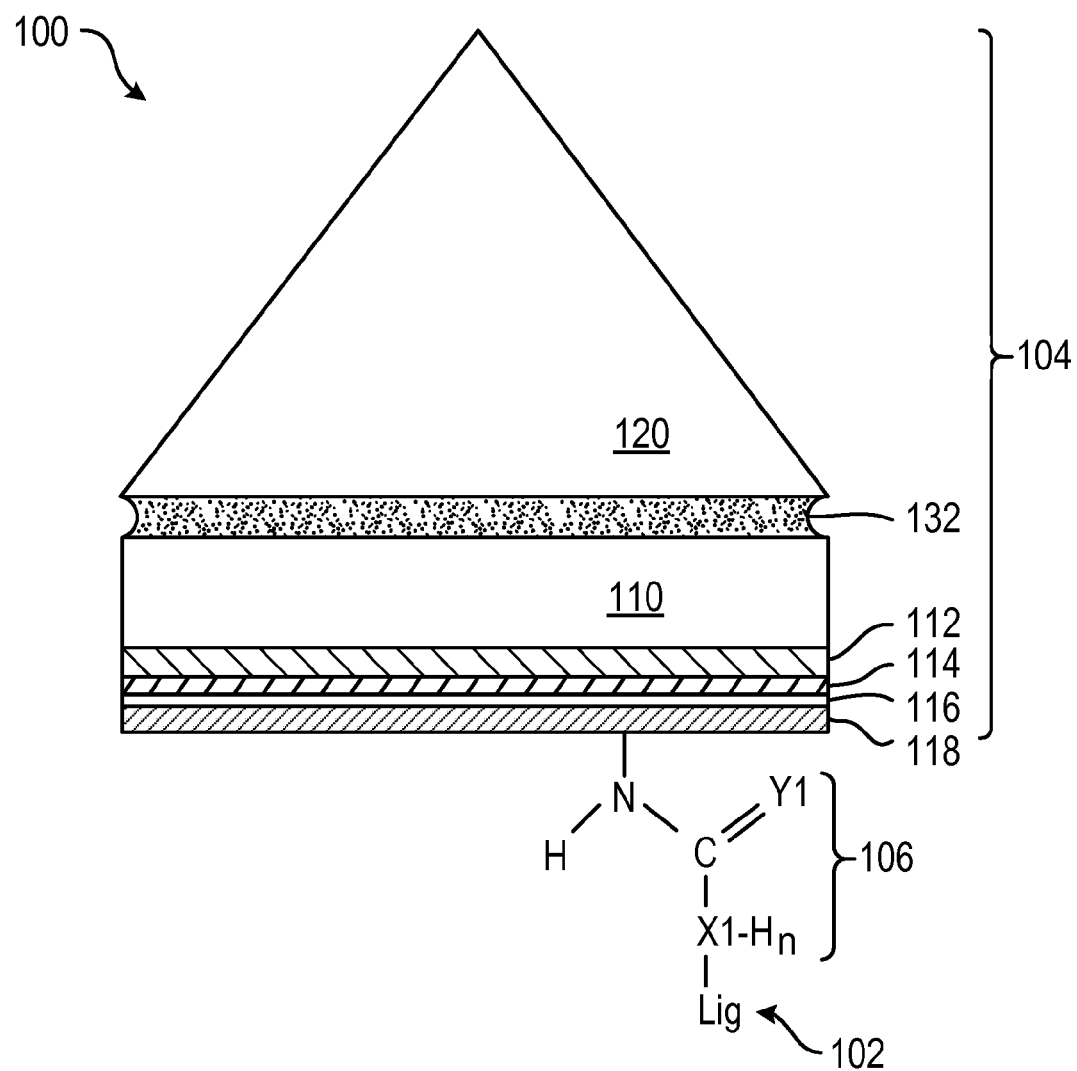

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It must be noted that, as used in the specification and the appended claims, the singular forms "a," "an" and "the" include plural referents unless the context clearly dictates otherwise. Thus, for example, reference to "a ligand" includes a plurality of ligands. It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation. In this specification and in the claims that follow, reference will be made to a number of terms that shall be defined to have the following meanings unless a contrary intention is apparent.

The term "sample" as used herein relates to a material or mixture of materials, typically, although not necessarily, in fluid form, e.g., aqueous or in solvent, containing one or more components of interest. Samples may be derived from a variety of sources such as from food stuffs, environmental materials, a biological sample such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

The term "analyte" is used herein to refer to a known or unknown component of a sample, which will specifically bind to a ligand on a substrate surface if the analyte and the ligand are members of a specific binding pair. In general, analytes are chemical molecules of interest, e.g., biopolymers, i.e., an oligomer or polymer such as an oligonucleotide, a peptide, a polypeptide, an antibody, or the like. In this case, an "analyte" is referenced as a moiety in a mobile phase (typically fluid), to be detected by a "ligand" which is bound to a substrate. However, either of the "analyte" or "ligand" may be the one which is to be evaluated by the other (thus, either one could be an unknown mixture of analytes, e.g., polypeptides, to be evaluated by binding with the other).

A "biopolymer" is a polymer of one or more types of repeating units, regardless of the source (e.g., biological (e.g., naturally-occurring, obtained from a cell-based recombinant expression system, and the like) or synthetic). Biopolymers may be found in biological systems and particularly include polypeptides and polynucleotides, including compounds containing amino acids, nucleotides, or a mixture thereof.

The terms "polypeptide" and "protein" are used interchangeably throughout the application and mean at least two covalently attached amino acids, which includes proteins, polypeptides, oligopeptides and peptides. A polypeptide may be made up of naturally occurring amino acids and peptide bonds, synthetic peptidomimetic structures, or a mixture thereof. Thus "amino acid", or "peptide residue", as used herein encompasses both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the D- or the L-configuration. The term "polypeptide" includes polypeptides in which the conventional backbone has been replaced with non-naturally occurring or synthetic backbones, and peptides in which one or more of the conventional amino acids have been replaced with one or more non-naturally occurring or synthetic amino acids. The term "fusion protein" or grammatical equivalents thereof references a protein composed of a plurality of polypeptide components, that while typically not attached in their native state, typically are joined by their respective amino and carboxyl termini through a peptide linkage to form a single continuous polypeptide. Fusion proteins may be a combination of two, three or even four or more different proteins. The term polypeptide includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, and the like.

In general, biopolymers, e.g., polypeptides or polynucleotides, may be of any length, e.g., greater than 2 monomers, greater than 4 monomers, greater than about 10 monomers, greater than about 20 monomers, greater than about 50 monomers, greater than about 100 monomers, greater than about 300 monomers, usually up to about 500, 1000 or 10,000 or more monomers in length. "Peptides" and "oligonucleotides" are generally greater than 2 monomers, greater than 4 monomers, greater than about 10 monomers, greater than about 20 monomers, usually up to about 10, 20, 30, 40, 50 or 100 monomers in length. In certain embodiments, peptides and oligonucleotides are between 5 and 30 amino acids in length.

The terms "ligand" and "capture agent" are used interchangeably herein and refer to an agent that binds an analyte through an interaction that is sufficient to permit the ligand to bind and concentrate the analyte from a homogeneous mixture of different analytes. The binding interaction is typically mediated by an affinity region of the ligand. Typical ligands include any moiety that can specifically bind to an analyte. In certain embodiments, a polypeptide (e.g., a monoclonal antibody or a peptide), a polynucleotide (e.g. DNA or RNA), a polysaccharide, or other biopolymer may be employed. Ligands usually "specifically bind" one or more analytes. Accordingly, "ligand" references a molecule or a multi-molecular complex which can specifically bind an analyte, e.g., specifically bind an analyte for the ligand, with a dissociation constant $K_D$ of less than about $10^{-4}$ M (e.g., typically less than about $10^{-5}$ M, more typically less than about $10^{-6}$ M) without binding to other targets.

The term "specific binding" refers to the ability of a ligand to preferentially bind to a particular analyte that is present in a homogeneous mixture of different analytes. Typically, a specific binding interaction will discriminate between desirable and undesirable analytes in a sample, typically more than about 10 to 100-fold or more (e.g., more than about 1000- or 10,000-fold). Typically, the affinity between a ligand and analyte when they are specifically bound in a ligand/analyte complex is characterized by a $K_D$ (dissociation constant) of less than about $10^{-4}$ M, $10^{-5}$ M, $10^{-6}$ M, $10^{-7}$ M, $10^{-8}$ M, $10^{-9}$ M, or $10^{-10}$ M, or even less.

The term "ligand/analyte complex" is a complex that results from the specific binding of a ligand with an analyte, i.e., a "binding partner pair". As used herein, "binding partners" and equivalents refer to pairs of molecules that can be found in a ligand/analyte complex, i.e., exhibit specific binding with each other. A ligand and an analyte for the ligand will usually specifically bind to each other under "conditions suitable for specific binding" (also referenced as "specific binding conditions"), where such conditions are those conditions (in terms of salt concentration, pH, detergent, protein concentration, temperature, etc.) which allow for binding to occur between ligands and analytes in solution. Such conditions, particularly with respect to proteins and nucleic acids are well known in the art (see, e.g., Harlow and Lane (Antibodies: A Laboratory Manual Cold Spring Harbor Laboratory, Cold Spring Harbor, N.Y. (1989) and Ausubel, et al., Short Protocols in Molecular Biology, 5th ed., Wiley & Sons, 2002). Conditions suitable for specific binding typically permit ligands and target pairs that have a dissociation constant $K_D$ of less than about $10^{-6}$ M to bind to each other, but not with other ligands or targets. "Hybridizing" and "binding", with respect to polynucleotides, are used interchangeably.

The phrase "surface-bound ligand" refers to a ligand that is immobilized on a surface of a solid substrate. Such "surface bound ligands" may be bound directly to the substrate or indirectly bound to the substrate, e.g. via one or more intermediate moieties (e.g. linking groups and/or a NCYX linker moiety) and/or layers of intermediate materials (e.g. gel materials). In certain embodiments, the ligands employed herein are present on a surface of the same substrate, e.g., a subject sensor.

The term "pre-determined" refers to an element whose identity is known prior to its use. For example, a "pre-determined analyte" is an analyte whose identity is known prior to any binding to a ligand. An element may be known by name, sequence, molecular weight, its function, or any other attribute or identifier. In some embodiments, the terms "desired analyte" or "analyte of interest", i.e., a known analyte that is of interest, is used synonymously with the term "pre-determined analyte".

The terms "antibody" and "immunoglobulin" are used interchangeably herein to refer to a ligand that has at least an epitope binding domain of an antibody. These terms are well understood by those in the field, and refer to a protein containing one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions. Types of antibodies, including antibody isotypes, monoclonal antibodies and antigen-binding fragments thereof (e.g., Fab, Fv, scFv, and Fd fragments, chimeric antibodies, humanized antibodies, single-chain antibodies, etc) are well known in the art and need not be described in any further detail.

An "array," includes any one, two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more arrays disposed on a surface of a substrate. Depending upon the use, any or all of the arrays may be the same or different from one another and each may contain multiple spots or features. A typical array may contain more than ten, more than one hundred, more than one thousand, more than ten thousand features, or even more than one hundred thousand features, in an area of less than 20 $cm^2$ or even less than 10 $cm^2$. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 $cm^2$, or even less than 50 $cm^2$, 10 $cm^2$ or 1 $cm^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either precursor units (such as amino acid or nucleotide monomers) in the case of in situ fabrication, or the previously obtained polymer. Such methods are described in detail in, for example, references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. Other drop deposition methods can be used for fabrication, such as are known in the art. Also, instead of drop deposition methods, photolithographic array fabrication methods may be used. Interfeature areas need not be present particularly when the arrays are made by photolithographic methods.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the binding of the targets by the probes is detected and recorded. For the purposes of this invention, the scan region includes the entire area of the slide scanned between the first feature of interest and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

The term "mixture", as used herein, refers to a combination of elements, e.g., binding agents or analytes, that are interspersed and not in any particular order. A mixture is homogeneous and not spatially separated into its different constituents. Examples of mixtures of elements include a number of different elements that are dissolved in the same aqueous solution, or a number of different elements attached to a solid support at random or in no particular order in which the different elements are not spatially distinct. In other words, a mixture is not addressable. To be specific, an array of ligands, as is commonly known in the art, is not a mixture of ligands because the species of ligands are spatially distinct and the array is addressable.

"Isolated" or "purified" generally refers to isolation of a substance (compound, polynucleotide, protein, polypeptide, polypeptide composition) such that the substance comprises a significant percent (e.g., greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

The term "assessing" includes any form of measurement, and includes determining if an element is present or not. The terms "determining", "measuring", "evaluating", "assessing" and "assaying" are used interchangeably and may include quantitative and/or qualitative determinations. Assessing may be relative or absolute. "Assessing the presence of" includes determining the amount of something present and/or determining whether it is present or absent.

A sensor "package" may contain only the sensor, although the package may include other features (such as a housing with a chamber). It will also be appreciated that throughout the present application, that words such as "top," "upper," and "lower" are used in a relative sense only.

A "computer-based system" refers to the hardware means, software means, and data storage means used to analyze data or other information in accordance with the invention. The minimum hardware of the computer-based systems typically comprises a central processing unit (CPU), input means, output means, and data storage means. A skilled artisan can readily appreciate that any one of the currently available computer-based system are suitable for use in embodiments in accordance with the invention. The data storage means may comprise any manufacture comprising a recording of the information as described above, or a memory access means that can access such a manufacture. To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc. A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

If one composition is "bound" to another composition, the compositions do not have to be in direct contact with each other. In other words, bonding may be direct or indirect, and, as such, if two compositions (e.g., a substrate and a ligand) are bound to each other, there may be at least one other composition (e.g., another layer) between those compositions. Binding between any two compositions described herein may be covalent or non-covalent. The terms "bound" and "linked" are used interchangeably herein. In the context of chemical structures, "bound" (or "bonded") may refer to the existence of a chemical bond directly joining two moieties or indirectly joining two moieties (e.g. via a linking group). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect.

A "prism" is a structure that is bounded in part by two nonparallel plane faces and is used to refract or disperse a beam of light. The term prism encompasses round, cylindrical-plane lenses (e.g., semicircular cylinders) and a plurality of prisms in contact with each other. A prism typically comprises a light transmissive material.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

The term "modified alkyl" refers to an alkyl group having from one to twenty-four carbon atoms, and further having additional groups, such as one or more linkages selected from ether-, thio-, amino-, phospho-, oxo-, ester-, and amido-, and/or being substituted with one or more additional groups including lower alkyl, aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. The term "modified lower alkyl" refers to a group having from one to six carbon atoms and further having additional groups, such as one or more linkages selected from ether-, thio-, amino-, phospho-, keto-, ester-, and amido-, and/or being substituted with one or more groups including lower alkyl; aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above.

The term "alkenyl" as used herein, unless otherwise specified, refers to a branched, unbranched or cyclic (e.g. in the case of C5 and C6) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to six carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to six carbon atoms, and includes, for example, acetylenyl and propynyl, and the term "cycloalkynyl" refers to cyclic alkynyl groups.

The term "aryl" as used herein refers to an aromatic species containing 1 to 5 aromatic rings, either fused or linked, and either unsubstituted or substituted with 1 or more substituents typically selected from the group consisting of lower alkyl, aryl, aralkyl, lower alkoxy, thioalkyl, hydroxyl, thio, mercapto, amino, imino, halo, cyano, nitro, nitroso, azide, carboxy, sulfide, sulfone, sulfoxy, phosphoryl, silyl, silyloxy, and boronyl; and lower alkyl substituted with one or more groups selected from lower alkyl, alkoxy, thioalkyl, hydroxyl thio, mercapto, amino, imino, halo, cyano, nitro, nitroso, azide, carboxy, sulfide, sulfone, sulfoxy, phosphoryl, silyl, silyloxy, and boronyl. Typical aryl groups contain 1 to 3 fused aromatic rings, and more typical aryl groups contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —(CH2)j-Ar wherein j is an integer in the range of 1 to 24, more typically 1 to 6, and Ar is a monocyclic aryl moiety.

"Moiety" and "group" are used to refer to a portion of a molecule, typically having a particular functional or structural feature, e.g. a linking group (a portion of a molecule connecting two other portions of the molecule), or an ethyl moiety (a portion of a molecule with a structure closely related to ethane).

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

"NCYX linker moiety", as referenced herein, refers to a linking group having the structure

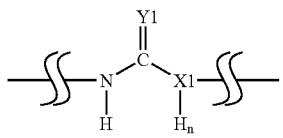

wherein:
Y1 is selected from O or S;
X1 is selected from O, N or S, provided that, if Y1 is S, X1 is N;
n equals 1 when X1 is N, or n equals 0 when X1 is S or O; and
the broken lines indicate the bonds via which the other portions of the molecule that are linked by the NCYX linker moiety are bound to the NCYX linker moiety. In the present invention, the "other portions of the molecule that are linked by the NCYX linker moiety" typically may include a sensor substrate, a ligand, a linking group bound to a ligand, a functional group for binding a ligand, or a linking group bound to a functional group for binding a ligand, as well as other groups apparent from the present disclosure. These groups may be bound directly to the linker or may be bound indirectly, i.e. via one or more intermediary groups.

"Functionalized" references a process whereby a material is modified to have a specific moiety bound to the material, e.g. a molecule or substrate is modified to have the specific moiety; the material (e.g. molecule or support) that has been so modified is referred to as a functionalized material (e.g. functionalized molecule or functionalized support).

The term "halo" or "halogen" is used in its conventional sense to refer to a chloro, bromo, fluoro or iodo substituent.

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group.

"Substituent" references a group that replaces another group in a chemical structure. Typical substituents include nonhydrogen atoms (e.g. halogens), functional groups (such as, but not limited to amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include alkyl, lower alkyl, aryl, aralkyl, lower alkoxy, thioalkyl, hydroxyl, thio, mercapto, amino, imino, halo, cyano, nitro, nitroso, azide, carboxy, sulfide, sulfone, sulfoxy, phosphoryl, silyl, silyloxy, boronyl, and modified lower alkyl.

A "group" includes both substituted and unsubstituted forms. Typical substituents include one or more lower alkyl, modified alkyl, any halogen, hydroxy, or aryl. Any substituents are typically chosen so as not to substantially adversely affect reaction yield (for example, not lower it by more than 20% (or 10%, or 5% or 1%) of the yield otherwise obtained without a particular substituent or substituent combination).

Hyphens, or dashes, are used at various points throughout this specification to indicate attachment, e.g. where two named groups are immediately adjacent a dash in the text, this indicates the two named groups are attached to each other. Similarly, a series of named groups with dashes between each of the named groups in the text indicates the named groups are attached to each other in the order shown. Also, a single named group adjacent a dash in the text indicates the named group is typically attached to some other, unnamed group. In some embodiments, the attachment indicated by a dash may be, e.g. a covalent bond between the adjacent named groups. In some other embodiments, the dash may indicate indirect attachment, i.e. with intervening groups between the named groups. At various points throughout the specification a group may be set forth in the text with or without an adjacent dash, (e.g. amido or amido-, further e.g. alkyl or alkyl-, yet further e.g. Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g. where a linkage is intended, such as linking groups).

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

Other definitions of terms appear throughout the specification.

The invention in particular embodiments provides an evanescent wave sensor which includes a ligand bound to a sensor substrate via a NCYX linker moiety. Methods of making the subject evanescent wave sensors are also provided which include contacting a first reactive moiety having the structure

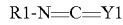
R1-N=C=Y1 with a second reactive moiety having the structure

R2-X1H$_m$ as further described below.

Also provided by the invention are methods in which a subject evanescent wave sensor is contacted with a sample, and binding of analytes in the sample to the sensor is assessed by evanescent wave detection. The invention also provides kits and systems for performing the subject methods. The invention finds use in a variety of applications in which it is desirable to detect analytes, e.g., drug discovery, environmental, and diagnostic applications, detecting post-translational modifications and point mutations, epitope mapping, and other applications.

In describing the invention in greater detail than provided above, the subject evanescent wave sensors are described first, followed by a description of an analyte detection system employing a subject evanescent wave sensor. Following this, a discussion of methods of using a subject evanescent wave sensor to detect an analyte will be presented. Finally, kits for performing the subject methods are described.

Evanescent Wave Sensors

As mentioned above, the invention provides an evanescent wave sensor having a ligand that is bound to a substrate via a NCYX linker moiety. With reference to FIG. 1, a subject sensor 100 is illustrated which includes ligand 102 bound to sensor substrate 104 via NCYX linker moiety 106. Sensor substrate 104 includes light transmissive support 110. Sensor substrate 104 has a surface to which one or more optional materials may be bound. In typical embodiments, such optional materials include metal layer 112, metal oxide layer 114, self-assembled monolayer 116, and polymer layer 118. The one or more optional materials, when present, may be bound to the light transmissive support in the order illustrated in FIG. 1 or may be present in any order that provides a functional evanescent wave sensor. NCYX linker moiety 106 is typically bound to the light transmissive support 110 of the sensor substrate 104 via the one or more optional materials in embodiments in which the one or more optional materials are present. Typically, NCYX linker moiety 106 is bound to the light transmissive support 110 of the sensor substrate 104 via at least one layer selected from a metal oxide layer 114, a glass layer, or a polymer layer 118, and in particular embodiments may also be bound to the light transmissive support 110 via a metal layer 112 and/or a self assembled monolayer (SAM) 116.

In certain embodiments, a subject sensor 100 includes a prism 120 (pictured in FIG. 1) or a grating disposed in operable relation to the light transmissive support 110. The light transmissive support 110 may be placed directly adjacent an edge of the prism 120 to receive light transmitted through the prism 120. As is well known, typically a refractive index-matching composition 132 (e.g. an oil or gel) is included between the light transmissive support 110 and prism 120 in such configurations. In certain embodiments, the light transmissive support is prism shaped, and the ligand 102 is bound to a surface of the prism-shaped light transmissive support via NCYX linker moiety 106 and any of the optional materials mentioned above and illustrated in FIG. 1. In certain embodiments, the sensor substrate 104 does not include a prism but is disposed adjacent an edge of a prism, typically with a refractive index-matching composition (e.g. an oil or gel) included between the sensor substrate 104 and prism in such configurations.

The light transmissive support 110 may have various shapes and/or sizes adapted to the intended use in the sensor substrate. The light transmissive support 110 typically has at least one planar surface, and in certain embodiments may have a plurality of planar surfaces. In an embodiment the light transmissive support 110 includes two planar surfaces that are parallel to each other, e.g. the light transmissive support 110 may include a planar support such as a glass slide. In various embodiments the light transmissive support may exist, for example, as sheets, tubing, filaments, pads, slices, films, strips, disks, etc. The light transmissive support is usually flat, but may take on alternative surface configurations.

The light transmissive support 110 comprises one or more materials which permit the transmission of light through the material; thus, the light transmissive support 110 typically comprises one or more materials selected from glass, quartz, silica, a polymeric material, such as an acrylic polymer, cyclic olefin, polyolefin, polydimethylsiloxane, polymethylmethyl acrylate, and/or a polycarbonate, where such materials allow the transmission of light through the materials. In certain embodiments, a light transmissive support has the characteristic of permitting at least about 2% of the light incident on the light transmissive support to be transmitted through the light transmissive support, typically at least 5%, at least 10%, at least 20%, at least 30%, at least 50%, at least 70%, at least 80%, at least 90%, or at least 95% of the light incident on the light transmissive support to be transmitted through the light transmissive support. In this regard, the "light incident on the light transmissive support" has a wavelength (or a range of wavelengths) in a range that is selected to be relevant to the operation of the sensor substrate. In particular embodiments, the light transmissive support is transmissive to light having a wavelength in the visible range (i.e. a wavelength selected from the range from about 400 nm to about 700 nm). In some embodiments, the light transmissive support is transmissive to light having a wavelength in the UV range (e.g. a wavelength selected from the range from about 280 nm to about 400 nm) or in the IR range (e.g. a wavelength selected from the range from about 0.7 μm to about 5 μm). In this context, "light transmissive support" specifically includes embodiments in which light may be reflected within the light transmissive support, embodiments in which light may be transmitted through the light transmissive support without being reflected, and embodiments in which a portion of the light may be reflected within the light transmissive support and a portion of the light may be transmitted without being reflected. In certain embodiments, the light transmissive support may be made of a dielectric material that is transmissive to light at wavelengths used for analyte detection using the subject sensor.

In certain embodiments, the light transmissive support may be made of a material having a refractive index (n) of about 1.3 to about 2.3, e.g., of about 1.4, about 1.5, about 1.6, about 1.7, about 1.8, about 1.9, about 2.0, about 2.1, or about 2.2, although in other embodiments the light transmissive support may be made of a material having a refractive index more or less than the recited values. In particular embodiments, the refractive index of the light transmissive support is matched to that of the sample to be analyzed using the subject methods; in alternate embodiments, the refractive index of the light transmissive support may be different from that of the sample to be analyzed, e.g. greater or less than that of the sample to be analyzed. Further, a layer of dielectric material (e.g., $TiO_2$ or $SiO_2$ or the like), of about 300-600 nm thickness (e.g., about 400 nm) may be present between metal layer 112, if present, and light transmissive support 110. Such dielectric materials and their use in evanescent wave sensors are well known in the art, and, used herein, may sharpen resonance peaks, serve as an adhesion layer, and protect any metal layer during fabrication.

As mentioned above, sensor substrate 104 has a surface to which one or more optional materials may be bound. In typical embodiments, such optional materials include metal layer 112, metal oxide layer 114, self-assembled monolayer 116, and polymer layer 118. A surface of the sensor substrate 104 may be coated in a layer of metal 112, usually a free electron metal such as, e.g., copper, silver, aluminum or gold, although other metals may be used, such as a metal selected from platinum, palladium, chromium, niobium, rhodium, and iridium, or other metal. As is well known in the art, different metals produce different resonance effects, and, as such, the choice of metal depends on the resonance effect desired. This metal coating may be produced using known methods, e.g., sputtering or coating. In particular embodiments, the thickness of the metal layer may be in the range from about 20 nm to about 60 nm, typically in the range from about 20 nm to about 120 nm, although the metal layer may be outside these ranges in some embodiments. In particular embodiments, the substrate is coated in gold, which is well known in surface plasmon resonance detectors. A metal grating, as is commonly used in certain surface plasmon resonance methods, may also be present in a subject sensor. In certain embodiments, more than one metal is present in the metal layer, e.g. the metal layer may include a first layer of one metal and another layer of a second metal.

The sensor substrate 104 may include a metal oxide layer 114, such as a $TiO_2$ or $SiO_2$ layer described above. In other embodiments, the metal oxide is an oxide of the metal that makes up a metal layer (e.g. a chrome oxide layer on a chrome metal layer), although in other embodiment, the metal oxide need not be an oxide of the metal that makes up a metal layer 114 and instead may be any metal oxide. In particular embodiments, the metal oxide layer is disposed on a metal layer, such as pictured in FIG. 1. The metal oxide layer may serve to protect the metal layer from exposure to reagents or samples during use of the sensor substrate 104, or may be included for any other reason. In particular embodiments, the metal oxide layer provides functional groups for binding further materials; for example, the sensor substrate may be provided which includes a glass or $SiO_2$ layer, thereby providing for use of well known methods for binding to glass surfaces, e.g. silane chemistry. This glass or $SiO_2$ layer will typically be less than about 50 nm thick, e.g. less than about 40 nm, 30 nm, 20 nm, 10 nm thick, and will typically be at least about 2 nm thick, although in certain embodiments the layer may have a thickness outside the given values. Note that this glass layer is distinct from the light transmissive support, e.g. in typical embodiments the glass layer is disposed on a metal layer which is disposed on the light transmissive support. In some embodiments, the sensor substrate includes a silicon nitride layer bound to the light transmissive support (e.g. about 50 to about 500 nm thick) in addition to the metal layer.

In forming the sensor substrate, the layers of materials (e.g. metal layers and/or metal oxide layer) bound to the light transmissive support may be formed via thin film vapor deposition in a vacuum chamber using evaporation and sputtering processes. Such processes can be used, for example, to deposit a thin layer of metal by vacuum deposition, plasma enhanced chemical vapor deposition or other means onto a light transmissive support, or any other known method to deposit the layers of materials may be used. Metal and oxide films can be applied to surfaces via solution phase reactions, such as immersion or spraying, or in controlled atmosphere based processes such as sputtering, evaporation, chemical vapor deposition, and plasma-enhanced chemical vapor deposition. These processes may be useful in forming the metal and oxide layers that may be present in sensor substrates taught herein. One method for forming a thin film comprising a metal oxide on a substrate by reactive sputtering is described in U.S. Pat. No. 5,827,409 to Iwata et al., wherein the method includes introducing gaseous argon and gaseous oxygen to a space in front of a cathode, the cathode comprising a target which comprises a metal to be deposited; and depositing a thin film comprising a metal oxide of the metal on the substrate while moving the substrate parallel to the front of the target. Formation of a metal oxide layer may also be accomplished by conversion of a portion of the metal on the surface of the metal layer to metal oxide via a chemical oxidation process. For example, U.S. Pat. No. 6,635,435 states that depositing a chromium layer and exposing it to an oxidizing environment will form a chrome oxide layer.

The sensor substrate may include further surface modification layers present on the light transmissive support between the light transmissive support and the ligand. Such surface modifications may include a self-assembled monolayer (SAM) 116 and/or a polymer layer 118. In certain embodiments the sensor substrate 104 may be modified by processes known in the art in order to render the surface more suitable for binding to a SAM 116 or for binding to a polymer layer 118, for example to present particular surface functional groups (chemical groups or moieties on the surface), such as hydroxyl groups, amino groups, or other chemical groups suitable for binding the SAM 116 or polymer layer 118 (either directly or indirectly, e.g. via a linking group). The SAM is typically a single molecular unit thickness, e.g. a single thickness of the monomer unit used to form the SAM, and hence can be regarded as essentially a two-dimensional film bound to the light transmissive support. The polymer layer is generally thicker than a SAM and in typical embodiments is permeable (allows solution molecules, e.g. a sample solution containing an analyte, to diffuse into the polymer layer). The polymer layer can thus be regarded as essentially a three-dimensional matrix bound to the light transmissive support. As such, in particular embodiments, the polymer layer provides for a three-dimensional matrix of ligands, the ligands bound at sites within the polymer layer via a NCYX linker moiety.

A known procedure for derivatizing a metal oxide surface uses an aminoalkyl silane derivative, e.g., trialkoxy 3-aminopropylsilane such as aminopropyltriethoxy silane (APS), 4-aminobutyltrimethoxysilane, 4-aminobutyltriethoxysilane, 2-aminoethyltriethoxysilane, and the like. APS reacts readily with the oxide and/or siloxyl groups on metal and silicon surfaces. APS provides primary amine groups that may be used to further modify the surface of the sensor substrate 104. Such a derivatization procedure is described in EP 0 173 356 B1. Methods of incorporating other organosilane coupling agents to functionalize the sensor substrate surface are described in, e.g., Arkins, Silane Coupling Agent Chemistry, Petrarch Systems Register and Review, Eds. Anderson et al. (1987) and U.S. Pat. No. 6,258,454. A surface optimized for in-situ synthesis of DNA arrays is described in U.S. Pat. No. 6,258,454. Other methods for treating the surface of a support will be apparent in view of the teachings herein.

The polymer layer may include hydrogel, sol-gel, organic polymers, and/or other polymers and will depend on the intended design and conditions for use of the sensor substrate. The possible polymers include hydrogel, for example, polysaccharide such as, e.g. agarose, dextran, carrageenan, alginic acid, starch, cellulose or derivatives thereof such as, for example, carboxymethyl derivatives. In certain embodiments, the possible polymers include an organic polymer such as e.g. poly(vinylalcohol), poly(vinylchloride), polyacrylic acid, polyacrylamide and polyethylene glycol. Methods of forming crosslinked dextran hydrogels on sensor surfaces are known, as described in U.S. Pat. No. 5,242,828; and Fong et al., Analytica Chimica Acta 456: 201-208 (2002). The polymer matrix, e.g hydrogel layer, if present, will typically be at least about 10 nm thick, e.g. at least about 20 nm thick, typically at least about 30 nm thick, more typically at least about 40 nm thick, still more typically at least about 50 nm thick, and typically will be less than about 800 nm thick, typically less than 1000 nm thick, more typically less than about 1500 nm thick, still more typically less than about 2000 nm thick, although in certain embodiments the polymer layer or the hydrogel layer may have a thickness outside these ranges. The polymer layer may be formed in place, e.g. via polymerization of monomers on a surface during manufacture of the sensor substrate. Other methods include depositing the polymer layer via spin casting, coating, molding, or any other method available in the art.

Accordingly, the present invention provides methods of making an evanescent wave sensor that include, in particular embodiments, obtaining a light transmissive support, disposing one or more layers selected from a metal layer, a metal oxide layer, a self-assembled monolayer, and a polymer layer to result in a sensor substrate, and then binding a ligand to the sensor substrate according to methods described herein.

Referring again to FIG. 1, a subject sensor 100 is illustrated which includes ligand 102 bound to sensor substrate 104 via NCYX linker moiety 106. The NCYX linker moiety has the structure (I):

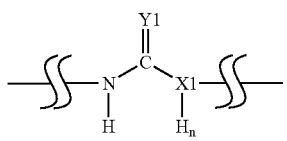
(I)

wherein:
Y1 is selected from O or S;
X1 is selected from O, N or S;
n equals 1 when X1 is N, or n equals 0 when X1 is S or O, provided that, if Y1 is S, X1 is N; and
the broken lines indicate sites where substituents may be bound to the indicated structure of structure (I). In embodiments of the present invention, the NCYX linker moiety is bound to (1) the sensor substrate (optionally via a linking group), (2) the ligand or a functional group for binding to the ligand (again, optionally via a linking group), as well as other groups apparent from the present disclosure. These groups may be bound directly to the NCYX linker moiety or may be bound indirectly, i.e. via one or more intermediary groups. The particular sites in structure (I) via which these elements are bound to the NCYX linker moiety will be evident from the description elsewhere herein, particularly the description relating to structure (II).

According to the present invention, the NCYX linker moiety may result from the reaction between a first reactive moiety having the structure

R1-N=C=Y1 with a second reactive moiety having the structure

R2-X1H$_m$

Thus, in certain embodiments of the present invention, a method is provided of making an evanescent wave sensor, wherein the method includes:
contacting a first reactive moiety having the structure

R1-N=C=Y1 with a second reactive moiety having the structure

R2-X1H$_m$ under conditions sufficient to result in covalent coupling of R1 to R2 via a NCYX linker moiety, wherein:
one of R1 or R2 is a sensor substrate;
the other of R1 or R2 is selected from a ligand, a linking group bound to a ligand, a functional group for binding a ligand, or a linking group bound to a functional group for binding a ligand;
Y1 is selected from O or S;
X1 is selected from O, N or S, provided that, if Y1 is S, X1 is N;
n equals 1 when X1 is N, or n equals 0 when X1 is S or O; and
m equals n plus 1.

Accordingly, the product of the above reaction of contacting the first reactive moiety with the second reactive moiety has the structure (II):

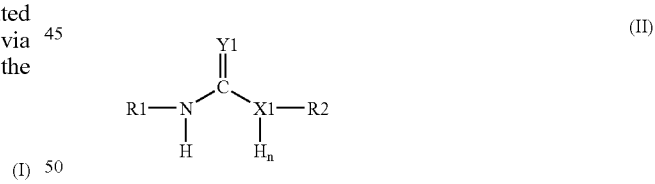
(II)

wherein R1, R2, Y1, X1, n and m are as described above.
[**]The first reactive moiety having the structure

R1-N=C=Y1 can be obtained by exemplary methods described herein, as well as by other methods known for providing an isocyanato moiety (or isothiocyanato moiety) as part of a larger structure. In one exemplary embodiment, a 2-5% solution of a silane compound such as 3-isocyanatopropyltriethoxysilane (available from United Chemical Technologies, Bristol, Pa. (# 17840)) in 95% ethanol is used to provide a modified silane layer having isocyanato moieties bound to a light transmissive support, e.g. via a SiO$_2$ layer bound to a metal layer which is bound to the light transmissive support. In certain embodiments, the first reactive moiety having the structure R1-N=C=Y1 may be obtained by treating an amine with phosgene or thiophosgene; see Chem. Soc. Rev. 3:209-230 (1974). Other exemplary (but non-limiting) methods include the treatment of alkyl halides with cyanate ions or performing a Curtius Rearrangement where an acyl halide is treated with sodium azide to give an acyl azide followed by pyrolysis to the isocyanate (see J. March in Advanced Organic Chemistry, $4^{th}$ ed. (John Wiley and Sons, New York). The selection of starting materials will depend on the identity and properties of the desired ligand and/or sensor substrate and will be apparent given the disclosure herein.

The second reactive moiety having the structure $R2-X1H_m$ can be obtained by exemplary methods described herein, as well as by other methods known for providing a hydroxyl, thiol, or amino moiety as part of a larger structure. In one exemplary embodiment, R2 is a ligand that inherently possesses the —$X1H_m$ moiety, such as a protein ligand having one or more available amino groups and/or thiol groups. In certain embodiments, the second reactive structure $R2-X1H_m$ is found in typical biological structures of interest, such as the terminal and epsilon-amino groups of peptides, proteins, antibodies, etc or the hydroxyl groups of sugars, or the thiol groups in known amino acids. Furthermore, the hydroxyl groups on saccharides or nucleosides may be used as the nucleophiles with the first reactive moiety. The selection of starting materials will depend on the identity and properties of the desired ligand and/or sensor substrate and will be apparent given the disclosure herein.

In certain embodiments of the present invention, a method is provided of making an evanescent wave sensor, wherein the method includes contacting a first reactive moiety which has an isocyanato (or isothiocyanato) moiety with a second reactive moiety which has an hydroxyl, thiol, or amino moiety. Typical conditions for the reaction are those that result in a NCYX linker moiety, and can include reaction of the first reactive moiety with the second reactive moiety under conditions including: gently refluxing solvents (e.g., 50-100 degrees Celsius) for a sufficient time to result in the product (e.g. about 1-3 hours). In typical embodiments, the product having an NCYX linker moiety is formed by addition of a nucleophilic structure (e.g. $R2-X1H_m$) to an isocyanate-containing or isothiocyanate-containing compound at temperature ranges from 4 degrees to 100 degrees over a period of 1-20 hours depending on the particular structures. In certain embodiments, the reactions can be done in aqueous solvents. In certain other embodiments, the reactions can be done in organic solvents.

A linking group, as a member of structures (I), (II) indicated above, may be any linking group that is compatible with the making and use of the sensors described herein, that is, does not significantly interfere with the making and use of the sensor. For example, the linking group may contain an unreactive alkyl chain, e.g., containing 3-12 carbon atoms. As described above, the "linking group bound to a ligand" typically has the structure -Lnk-Lig wherein Lnk is a linking group and Lig is the ligand, and the ligand is bound to the NCYX linker moiety via the linking group. Similarly, the "linking group bound to a functional group for binding a ligand" has the structure -Lnk-Fn wherein Lnk is a linking group and Fn is a functional group for binding a ligand, and the functional group for binding a ligand is bound to the NCYX linker moiety via the linking group. In particular embodiments the functional group for binding a ligand is any moiety that participates in binding a ligand to the sensor substrate, e.g. by reacting chemically to form a covalent bond. Accordingly, the present invention provides methods in which the ligand is bound to the NCYX linker moiety by contacting a sensor substrate to which a functional group is bound via a NCYX linker moiety with a ligand under conditions which result in the ligand being bound to the sensor substrate via the NCYX linker moiety. The nature of the functional group is not essential to the present invention, as any known coupling chemistry compatible with the sensor substrate (i.e. which doesn't result in degradation of the sensor substrate) may be used to couple to the ligand. As such, various strategies of coupling ligands to substrates using functional groups on the substrates are known in the art and may be employed advantageously in the disclosed methods. Typical strategies require a complementary reactive group on the ligand or are selected based on moieties already present on the ligand (e.g. amino groups of peptides).

The ligand may be any moiety that specifically binds an analyte through an interaction that is sufficient to permit the ligand to bind and concentrate the analyte from a homogeneous mixture of different analytes. The binding interaction is typically mediated by an affinity region of the ligand. The ligand typically is selected based on its ability to bind to the desired analyte, e.g. the ligand may be a moiety capable of binding to one or more of food stuffs, environmental materials, a biological sample such as tissue or fluid isolated from an individual (including but not limited to, for example, plasma, serum, spinal fluid, semen, lymph fluid, the external sections of the skin, respiratory, intestinal, and genitourinary tracts, tears, saliva, milk, blood cells, tumors, organs), and also samples of in vitro cell culture constituents (including but not limited to conditioned medium resulting from the growth of cells in cell culture medium, putatively virally infected cells, recombinant cells, cell components, and cell fragments). In certain embodiments, the ligand may be a moiety isolated from food stuffs, environmental materials, a biological sample such as tissue or fluid isolated from an individual (including but not limited to, for example, plasma, serum, spinal fluid, semen, lymph fluid, the external sections of the skin, respiratory, intestinal, and genitourinary tracts, tears, saliva, milk, blood cells, tumors, organs), and also samples of in vitro cell culture constituents (including but not limited to conditioned medium resulting from the growth of cells in cell culture medium, putatively virally infected cells, recombinant cells, cell components, and cell fragments).

In particular embodiments, the ligand is a biopolymer. In certain embodiments, the ligand may be a polypeptide, e.g., an antibody, a peptide, a protein, an enzyme, a fragment thereof. In certain other embodiments the ligand may be a polynucleotide, e.g. an RNA fragment, a DNA fragment, an oligonucleotide, or a synthetic mimetic of a polynucleotide (e.g. a peptidonucleic acid "PNA" or other modified nucleic acids well known in the art). In certain embodiments the ligand may be an antigen or an antibody. In some embodiments, the ligand may be a cell, a cell fragment, a bacterium, a spore, a virus, or a virion. In some embodiments, the ligand may be a drug compound or an organic compound known to specifically bind to an analyte. In particular embodiments, a plurality of different ligands may be present on a sensor substrate, wherein the ligands may be selected from any of the species of ligand indicated herein. In some embodiments, the ligand may be an avidin or biotin moiety, allowing the further functionalization of the sensor substrate with a secondary ligand. In such embodiments the secondary ligand would be bound to the NCYX linker moiety via a biotin/avidin linkage, e.g. which may be formed by, e.g. contacting a secondary ligand bound to an avidin with biotin bound to a sensor substrate via a NCYX linker moiety to result in the secondary ligand bound the sensor substrate via the biotin/avidin linkage and the NCYX linker moiety. In such embodiments, the secondary ligand may be any of the possibilities discussed above for the ligand, where such possibilities yield a functional sensor. One potential advantage of such an embodiments is that the sensor substrate functionalized with, e.g. the avidin moiety, may be supplied in conjunction with a selection of, e.g. biotin-modified secondary ligands, and the end-user may select which secondary ligand to use. Alternatively, the sensor substrate functionalized with, e.g. the avidin moiety, may be supplied with a kit for modifying the secondary ligand, e.g. a kit for biotinylating a polypeptide. Various alternate embodiments will be apparent in light of the present disclosure. In particular embodiments, a moiety equivalent to the avidin may be used in place of the avidin, such as streptavidin or other known equivalents which readily bind to biotin. As an example, a biotinylated ligand may be contacted with a sensor substrate bound to streptavidin or avidin and incubated a suitable amount of time (e.g., 15-30 minutes) in a buffer with gentle mixing. The biotinylated ligand thereby becomes bound to the streptavidin. The bound ligand may be washed in phosphate buffered saline (PBS) or other suitable buffer, and the resulting ligand-bound sensor substrate may then be employed in an evanescent wave sensing method for detecting an analyte in a sample.

As will be recognized by one of skill in the art, ligands can be pre-made (e.g., isolated from a source, synthesized by a machine, or made by recombinant means) and then be bound to the sensor substrate via the NCYX linker moiety. Alternatively, ligands may be synthesized in situ on the sensor substrate; in such embodiments, an active group (e.g. a nucleotide monomer moiety) is bound to the sensor substrate via the NCYX linker moiety and serves as an initial site for in situ synthesis of the full ligand. In situ methods of synthesis of oligonucleotides are known in the art, such as described in WO 98/41531 and the references cited therein; in Caruthers (1985) Science 230: 281-285; Itakura et al., Ann. Rev. Biochem. 53: 323-356; Hunkapillar et al. (1984) Nature 310: 105-110; and in "Synthesis of Oligonucleotide Derivatives in Design and Targeted Reaction of Oligonucleotide Derivatives", CRC Press, Boca Raton, Fla., pages 100 et seq.; U.S. Pat. No. 4,458,066; U.S. Pat. No. 4,500,707; U.S. Pat. No. 5,153,319; U.S. Pat. No. 5,869,643; EP 0294196, and elsewhere.

In particular embodiments, the sensor substrate has a plurality of sites on the sensor substrate surface, each site having a different ligand bound thereto via a NCYX linker moiety. In such embodiments, the subject evanescent wave sensor presents an array of ligands. Such an array has a plurality of features, each of the plurality of features having a respective ligand bound to the sensor substrate, each of the plurality of features being addressably located at a respective site on the sensor substrate. Monitoring of multiple different analytes in a sample may be determined by an array of different ligands, each ligand having a specific response to a particular analyte. Ligands can, for example, be bound to the surface of a metal film on a sensor substrate via a NCYX linker moiety. In certain embodiments, the ligands can be bound, for example, through covalent binding via a NCYX linker moiety to a suitable polymer film (e.g. hydrogel) that is a few hundred nanometers thick (e.g. in the range from about 100 nm to about 1500 nm, typically about 200 nm to about 1000 nm) coating the metal film. The ligands can be biological, biochemical or chemical recognition elements or a combination of these elements. Depending on applications, various ligand-analyte interactions have been reported including antibody-antigen reactions, arrays of oligonucleotides or probes originating from cDNA libraries for DNA hybridization analysis, molecular imprinting techniques, ionic interaction with ionophores and chromo-ionophores, and electrochemical interaction where the metal film acts as one of the two electrodes (the cathode or the anode). Although these ligands are very different in nature, they have the inherent property that they all make use of surface or interface sensitive biochemical interactions, and these interactions can quantitatively be monitored using an evanescent wave sensing scheme. Such arrays of ligands bound to sensor substrates can be produced using any known method, e.g. drop deposition methods such as inkjet deposition methods, to deposit ligand-containing solutions onto a sensor substrate in accordance with methods described herein.

A subject evanescent wave sensor may be adapted for use in a particular type of detection method, e.g., a surface plasmon resonance method, and, as such, may be dimensioned and made of materials suitable for that method. Since many evanescent wave detection methods are generally well known in the art (e.g., surface plasmon resonance, grating coupler surface plasmon resonance, resonance mirror sensing and waveguide sensor interferometry using Mach-Zender or polarimetric methods, direct and indirect evanescent wave detection methods, etc.), one of skill in the art would know how to adapt a subject sensor for use in particular method without undue effort. See, e.g. Homola, J., et al., Sensors and Actuators B 54: 3-15 (1999); Welford, K., Opt. Quant. Elect. 23:1 (1991); Raether, H., Physics of Thin Films 9: 145 (1977); Myszka, J. Mol. Rec. 12:390-408 (1999); and Biomolecular Sensors, edited by Gizeli and Lowe. Taylor & Francis (2002). Exemplary surface plasmon resonance methods will be described in greater detail below, although it should be understood that such methods may be adapted to evanescent wave detection techniques other than SPR without undue experimentation given the description herein.

Analyte Detection Systems

As noted above, in particular embodiments the invention provides an analyte detection system. Referring to the exemplary embodiment illustrated in FIG. 2, the system contains a subject evanescent wave sensor 100 disposed in operable relation to an optical detection system 130. The evanescent wave sensor 100, described in greater detail above, includes metal layer 112 bound to the light transmissive support 110 and, optionally, one or more additional layers 113 bound to the light transmissive support 110, as described above. In particular embodiments, such optional additional layers may be selected from a metal oxide layer, a glass layer, a polymer layer, or combinations thereof. Ligand 102 is bound to the light transmissive support via the NCYX linker moiety 106. The evanescent wave sensor 100 is disposed adjacent prism 120 with a refractive index-matching composition 132 (e.g. an oil or gel) disposed between evanescent wave sensor 100 and prism 120. A housing 134 defines a fluid-tight chamber 136 in which ligand 102 is exposed. Sample is introduced into chamber 136 via fluid inlet 138 and exits chamber 136 via fluid outlet 140. Fluid inlet 138 and fluid outlet 140 are typically in fluid communication with appropriate fluid feeds and valves to control the flow of liquid sample into and out of the chamber 136, to facilitate washing of the ligands, to allow removal of undesirable materials from the chamber, and for system flushing, etc. Depending on the design of the analyte detection system, housing 134 may be an integral part of the sensor substrate or may be attached to the sensor substrate, allowing for replacement of the sensor substrate and housing as a unit, although other configurations are possible and will be apparent given the description herein.

Optical detection system 130 typically includes light source 142 and optical detector 144 that are interfaced to and under the control of a microprocessor 146 and suitable software. Microprocessor 146 may be part of a computer-based system. Programming for operating the system may be loaded onto the system, or a computer/microprocessor may be pre-programmed to run with the same. Light source 142 may be a wavelength-tunable laser or other light source typically known in the art for use in evanescent sensing applications. The light source typically provides light having a wavelength of between about 400 nm to about 2.0 µm when used in the subject methods. In particular embodiments, the wavelength of light used is from about 0.6 to about 1.2 µm, e.g., 0.7 µm to about 1.0 µm. In certain embodiments, the light used is monochromatic light, and the light may be polarized, and in certain embodiments, the wavelength of light used may change, i.e., may "sweep" during reading of a sensor. Accordingly, in some embodiments, the light used may not have a static wavelength. In typical embodiments, the wavelength may sweep between two different wavelengths separated by about 100 nm, about 200 nm, about 300 nm or about 400 nm or more, with the lower wavelength being any of the wavelengths listed above.

In use, a light beam 150 is directed toward prism 120 by way of various optics, generally including a collimator. The beam passes into and through light transmissive support 110 and reflects off metal layer 112. Reflected light 152 is collected in optical detector 144, and a corresponding signal is passed to the microprocessor 146, which collects data about the signal. The ligand 102 exposed in the chamber 136 may be contacted with sample and may bind to analytes in the sample, causing a change in the reflected light 152 that can be detected by optical detection system 130. In this manner, the analyte detection system may be employed to detect binding of an analyte to a ligand by detecting an evanescent wave. In certain embodiments, a collimated beam of light of varying wavelength may be used, and a compound metal oxide semiconductor (CMOS) imager or a charge coupled device (CCD) imager may be used in collecting the reflected light and in generating corresponding signals. In this manner, data for an entire sensor or for selected sections of a sensor can be collected simultaneously.

Methods of Detecting Analytes

A subject evanescent wave sensor may be employed in a method of detecting an analyte in which an analyte is bound to a subject evanescent wave sensor and detected thereby. In many embodiments, this method includes: a) contacting a sample with a subject evanescent wave sensor, and b) assessing the presence of an analyte bound to the sensor by detecting an evanescent wave. In use, a subject analyte detection system may be employed to detect an analyte by binding of the analyte to a ligand on a sensor substrate. In greater detail, the invention provides a method for assessing the presence of an analyte in a sample, comprising: a) contacting a sample with a ligand that is bound to a sensor substrate of an evanescent wave sensor, wherein the ligand is characterized as being capable of specifically binding to the analyte; and b) assessing the presence of the analyte on the sensor substrate by detecting an evanescent wave.

In general, the subject methods involve contacting a subject sensor with a sample under specific binding conditions and assessing binding of the ligands of the sensor to analytes in the sample by evanescent wave detection. In certain embodiments, an evanescent wave is detected by reflecting light off a metal layer, and detecting the angle and/or intensity of the reflected light. In other embodiments, a graphical image of the sensor surface may be produced. Binding of an analyte to ligands present on the sensor substrate can be detected by evaluating changes in reflected light angle and/or intensity, or changes in the graphical image, for example.

Specific analyte detection applications of interest include hybridization assays in which the nucleic acid ligands are employed and protein binding assays in which polypeptide ligands, e.g., antibodies or peptides, are employed. In these assays, a sample is first prepared and following sample preparation, the sample is contacted with a subject sensor under specific binding conditions, whereby complexes are formed between target nucleic acids or polypeptides (or other molecules) that specifically bind to ligands (e.g. nucleic acid probe sequences) attached to the sensor substrate. The presence of complexes is then detected, for example, using SPR methods or other evanescent wave detection methods.

In particular embodiments, a subject sensor may be used in surface plasmon resonance (SPR) methods. Protocols for carrying out SPR assays are well known to those of skill in the art and need not be described in great detail here. Generally, the sample suspected of comprising the analyte of interest is contacted with a subject sensor under conditions sufficient for the analyte to bind to its respective ligand that is present on the sensor. Thus, if the analyte of interest is present in the sample, it binds to the sensor at the site of its complementary ligand and a complex is formed on the sensor surface. The presence of this analyte/ligand binding complex on the surface of the sensor is then detected using SPR.

SPR may be achieved by using the evanescent wave that is generated when a laser beam, linearly polarized parallel to the plane of incidence, impinges onto a prism coated with a thin metal film (the metal layer). SPR is most easily observed as a change in the total internally reflected light just past the critical angle of the prism. This angle of minimum reflectivity (denoted as the SPR angle) shifts to higher angles as material is adsorbed onto the metal layer. The shift in the angle can be converted to a measure of the thickness of the adsorbed or added material by using complex Fresnel calculations and can be used to detect the presence or absence of analytes bound to the ligands on top of the metal layer. As is well known, SPR may be performed with or without a surface grating (in addition to the prism). Accordingly a subject sensor may contain a grating, and may be employed in other SPR methods other than that those methods explicitly described in detail herein.

In using SPR to test for binding between agents, a beam of light from a laser source is directed through a prism onto a subject sensor containing a light transmissive support, which has one external surface covered with a thin layer of a metal, to which in turn is bound a ligand that binds an analyte, as discussed above. The SPR angle changes upon analyte binding to the ligand. By monitoring either the position of the SPR angle or the reflectivity at a fixed angle near the SPR angle, the presence or absence of an analyte in the sample can be detected.

Various types of equipment for using SPR with a biosensor for biological or biochemical or chemical substances are known in the art (and described by Liedberg et al. (1983) Sensors and Actuators 4:299, European Patent Application 0305108 and U.S. Pat. No. 5,374,563, etc.), including grating coupled systems, optical waveguide systems and prism coupled attenuated total reflection systems.

In certain embodiments, a light source (typically a monochromatic light source) is used to illuminate the prism/metal layer at an incident angle that is near the SPR angle, and the reflected light is detected at a fixed angle with a CCD camera to produce an SPR image. The SPR image arises from variations in the reflected light intensity from different parts of the sensor substrate; these variations are created by any changes in organic film thickness or changes in index of refraction that occur upon adsorption onto the ligand-bound metal surface. SPR imaging is sensitive only to molecules in proximity to the surface, therefore unbound molecules remaining in solution do not interfere with in situ measurements.

In certain embodiments, the angles of incidence and reflection are "swept" together through the resonance angle, and the light intensity is monitored as function of angle. Very close to the resonance angle, the reflected light is strongly absorbed, and the reflected light becomes strongly reduced. In other embodiments, the source and detector angles are fixed near the resonance angle at an initial wavelength, and the wavelength is swept to step the resonance point through the fixed angle. The beam is collimated and an entire image of the substrate is captured.

Figure 2:
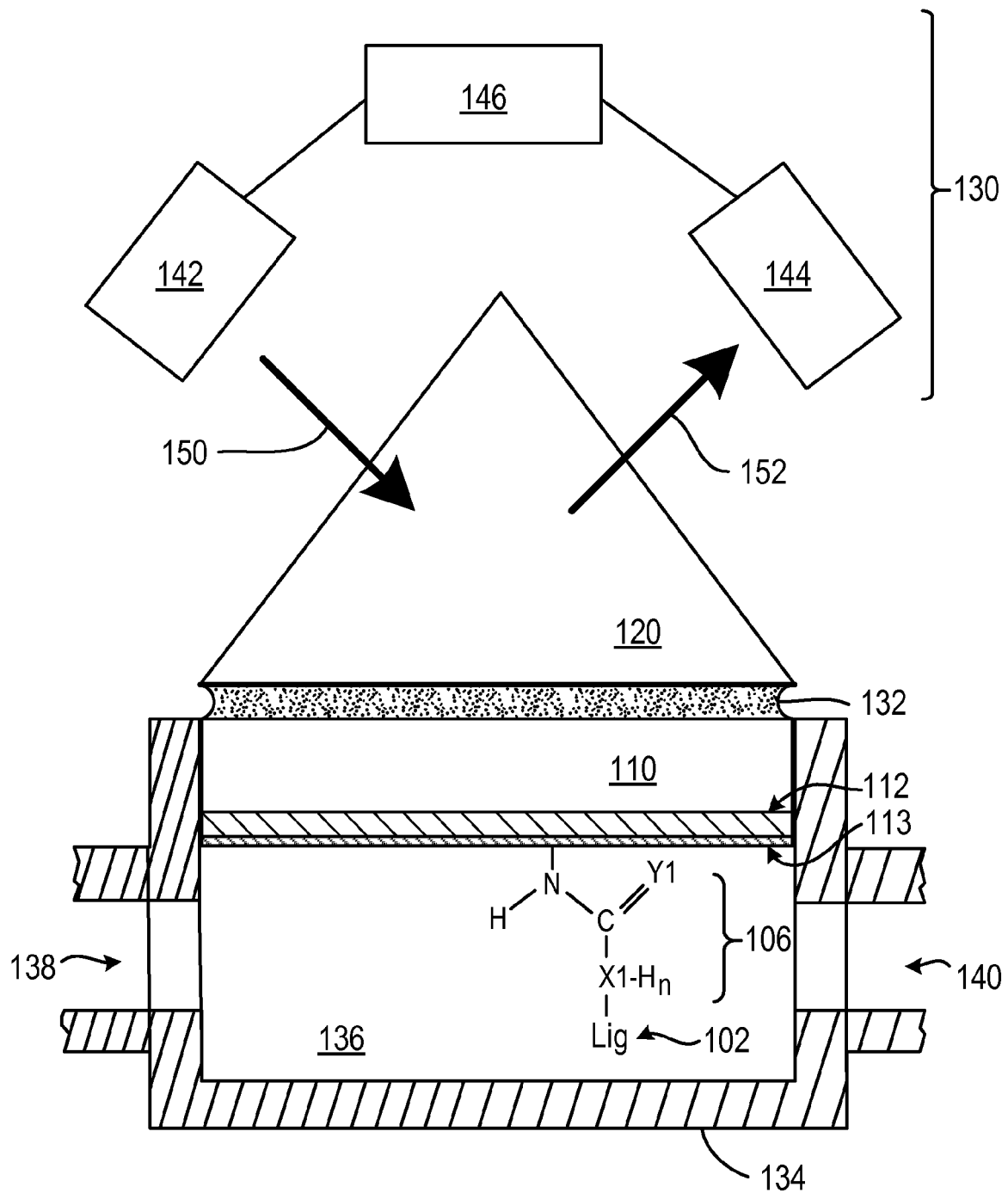
FIG. 2 depicts an embodiment of an analyte detection system including an evanescent wave sensor in accordance with the present invention.

One embodiment of this method may be described with reference to the embodiment shown in FIG. 2. As noted above, ligands 102 are bound to the sensor substrate 104 in the chamber 136. A liquid sample of interest is introduced into chamber 136. Analytes in the sample bind to ligands 102 which exhibit specific binding for those analytes. As a greater number of analyte molecules become bound thereto, their mass concentration increases, resulting in a detectable shift in the reflected light 152, typically detected as a change in light intensity and/or change in a light reflectance angle "θ" where light intensity maximizes, minimizes, or varies. Reflected light 152 is collected in optical detector 144, and a corresponding signal is passed to the microprocessor 146, which collects data about the signal. A sensor reader is used to accomplish the task of obtaining data from a subject sensor, which readers are generally well known in the art (see U.S. Pat. No. 6,466,323, for example). The data is then analyzed to assess the presence of analyte in the sample.

Results from reading a subject sensor may be raw results or may be processed results such as obtained by applying saturation factors to the readings, rejecting a reading which is above or below a predetermined threshold and/or any conclusions from the results (such as whether or not a particular analytes may have been present in the sample). The results of the reading (processed or not) may be forwarded (such as by communication) to a remote location if desired, and received there for further use (such as further processing). Stated otherwise, in certain variations, the subject methods may include a step of transmitting data to the remote location for further evaluation and/or use. Any convenient telecommunications means may be employed for transmitting the data, e.g., facsimile, modem, internet, etc. Alternatively, or in addition, the data representing results may be stored on a computer-readable medium of any variety such as is known. Retaining such information may be useful for any of a variety of reasons as will be appreciated by those with skill in the art.

Kits

Also provided by the subject invention are kits for practicing the subject methods, as described above. In certain embodiments, the subject kits at least include a sensor substrate having either of a first reactive moiety or a second reactive moiety bound thereto and regents to provide for functionalizing a ligand with the other of the first reactive moiety or the second reactive moiety, where the first reactive moiety has an isocyanato (or isothiocyanato) moiety and the second reactive moiety has an hydroxyl, thiol, or amino moiety, provided that, if the first reactive moiety has an isothiocyanato moiety, the second reactive moiety has an amino moiety. Such a kit may also include instructions for performing a reaction to functionalize the ligand and then to react the sensor substrate with the functionalized ligand to result in the ligand being bound to the sensor substrate via a NCYX linker moiety. In certain embodiments, the subject kits may include a sensor substrate and a ligand already bound to the sensor substrate via a NCYX linker moiety. In particular embodiments, the subject kits may also include reagents for preparing samples and/or refractive index-matching compositions for use with the sensor substrate. The kits may also include one or more control analyte mixtures, e.g., two or more control analytes for use in testing the kit. The various components of the kit may be present in separate containers or certain compatible components may be pre-combined into a single container, as desired.

In addition to above-mentioned components, the subject kits typically further include instructions for using the components of the kit to practice the subject methods. The instructions for practicing the subject methods are generally recorded on a suitable recording medium. For example, the instructions may be printed on a medium, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable medium included in the kit.

EXAMPLES

The practice of the present invention will employ, unless otherwise indicated, conventional techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

Preparation of Isocyanato-Coated Slides:

Gold-coated glass slides (titanium adhesion layer of 50 Angstroms (A) and evaporated gold of 460 A) are further treated via plasma-enhanced chemical vapor deposition (PECVD) to have a layer of 3200 A of silicon nitride followed with 150 A of silicon dioxide. This dielectric-coated slide is placed into a 2% ethanolic solution of 3-isocyanatopropyltriethoxysilane (#I7840, United Chemical Technologies, Inc.) for 12 hours. The slide is rinsed with dry ethanol, dried under a stream of nitrogen, and further cured at 90 degrees Celsius for 2 hours.

Attachment of Ligand to Isocyanato-Coated Slide:

A ligand compound containing appropriate nucleophilic groups ($—NH_2$, $—SH$ or $—OH$) is placed in aqueous alkaline solution (0.1M sodium carbonate, pH 9) and poured over the isocyanato-coated slide. Reaction is allowed to proceed at room temperature for 20 hours with gentle agitation. The slide is then washed thoroughly with deionized water and dried under nitrogen to yield the finished slide.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties, provided that if there is a conflict in definitions the definitions explicitly set forth herein shall control.

What is claimed is:

1. A method of making a sensor, the method comprising contacting a first reactive moiety having the structure

R1-N=C=Y1 with a second reactive moiety having the structure

R2-X1H$_m$ under conditions sufficient to result in a compound having the structure

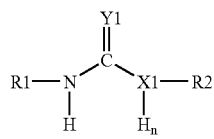

wherein:
one of R1 or R2 is a sensor substrate;
the other of R1 or R2 is selected from a ligand, a linking group bound to a ligand, a functional group for binding a ligand, or a linking group bound to a functional group for binding a ligand;
Y1 is selected from O or S; X1 is selected from N or S, provided that, if Y1 is S, X1 is N;
n equals 1 when X1 is N, or n equals 0 when X1 is S; and
m equals n plus 1.

2. A method according to claim 1, wherein the ligand is selected from an antibody, an antigen, a protein, a polynucleotide, a cell, a cell fragment, a bacterium, a spore, a virus, or a virion.

3. A method according to claim 1, wherein the sensor substrate comprises a light transmissive support.

4. A method according to claim 3, wherein the sensor substrate comprises a metal layer bound to the light transmissive support.

5. A method according to claim 4, wherein the metal layer comprises a metal selected from copper, silver, aluminum, gold, platinum, palladium, chromium, niobium, rhodium, or iridium.

6. A method according to claim 4, wherein the sensor substrate comprises a glass layer bound to the metal layer.

7. A method according to claim 3, wherein the sensor substrate comprises a metal oxide layer bound to the light transmissive support.

8. A method according to claim 3, wherein the sensor substrate comprises a self assembled monolayer bound to the light transmissive support.

9. A method according to claim 3, wherein the sensor substrate comprises a polymer layer bound to the light transmissive support.

10. A method according to claim 3, wherein the sensor substrate further comprises a linking group via which the light transmissive support is bound to either the —N=C=Y1 or the —X1H$_m$.

11. A method according to claim 3, wherein the light transmissive support comprises one or more materials selected from glass, quartz, silica, a polymeric material, an acrylic polymer, a cyclic olefin, a polyolefin, a polydimethylsiloxane, a polymethylmethyl acrylate, and a polycarbonate.

12. A method according to claim 1, wherein R1 is the sensor substrate, the sensor substrate comprises a light transmissive support bound to a linking group, and the —N=C=Y1 group is bound to the light transmissive support via the linking group.

13. A sensor having the structure:

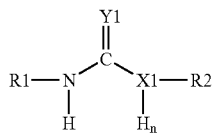

wherein:
one of R1 or R2 is a sensor substrate;
the other of R1 or R2 is selected from a ligand, a linking group bound to a ligand, a functional group for binding a ligand, or a linking group bound to a functional group for binding a ligand;
Y1 is selected from O or S;
X1 is selected from N or S, provided that, if Y1 is S, X1 is N;
n equals 1 when X1 is N, or n equals 0 when X1 is S.

14. A sensor according to claim 13, wherein the ligand is selected from an antibody, an antigen, a protein, a polynucleotide, a cell, a cell fragment, a bacterium, a spore, a virus, a virion, a drug compound, or an organic compound.

15. A sensor according to claim 13, wherein the sensor comprises a plurality of different ligands bound to the sensor substrate, each of the plurality of different ligands bound to the sensor substrate at a different site.

16. A sensor according to claim 13, wherein the sensor comprises an array having a plurality of features, each of the plurality of features having a respective ligand bound to the sensor substrate, each of the plurality of features being addressably located at a respective site on the sensor substrate.

17. A sensor according to claim 13, wherein the sensor substrate comprises a light transmissive support.

18. A sensor according to claim 17, wherein the sensor substrate further comprises a metal layer bound to the light transmissive support.

19. A sensor according to claim 18, wherein the metal layer comprises a metal selected from copper, silver, aluminum, gold, platinum, palladium, chromium, niobium, rhodium, or iridium.

20. A sensor according to claim 18, wherein the sensor substrate comprises a glass layer bound to the metal layer.

21. A sensor according to claim 17, wherein the sensor substrate comprises a metal oxide layer bound to the light transmissive support.

22. A sensor according to claim 17, wherein the sensor substrate comprises a self assembled monolayer bound to the light transmissive support.

23. A sensor according to claim 17, wherein the sensor substrate comprises a polymer layer bound to the light transmissive support.

24. A sensor according to claim 17, wherein the sensor substrate further comprises a linking group via which the light transmissive support is bound to the ligand.

25. A system comprising:

a sensor comprising the structure:

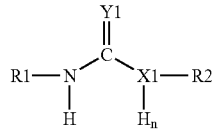

wherein:

one of R1 or R2 is a sensor substrate;

the other of R1 or R2 is selected from a ligand, a linking group bound to a ligand, a functional group for binding a ligand, or a linking group bound to a functional group for binding a ligand;

Y1 is selected from O or S;

X1 is selected from N or S, provided that, if Y1 is S, X1 is N; and n equals 1 when X1 is N, or n equals 0 when X1 is S; and a light source.

* * * * *